United States Patent [19]

Lapinski et al.

[11] 4,172,224
[45] Oct. 23, 1979

[54] PROCESS FOR THE DETECTION OF MICRO-CRACKS

[75] Inventors: Norman Lapinski, Chicago; Allen Sather, Plainfield, both of Ill.

[73] Assignee: The United States of America as represented by the United States Department of Energy, Washington, D.C.

[21] Appl. No.: 954,380

[22] Filed: Oct. 24, 1978

[51] Int. Cl.$^2$ .............................................. G09K 3/00
[52] U.S. Cl. .................................. 250/302; 250/321; 250/323; 250/358 R
[58] Field of Search ........... 250/320, 321, 323, 358 R, 250/359, 360, 322, 302; 424/4

[56] References Cited

U.S. PATENT DOCUMENTS 3,704,370  11/1972  Shelton ................................ 250/302

OTHER PUBLICATIONS

H. Berger, "Practical Applications of Neutron Radiography and Gaging", ASTM Special Technical Publication 586, pp. 10–15, pp. 268–273.

*Primary Examiner*—Craig E. Church
*Assistant Examiner*—Thomas P. O'Hare
*Attorney, Agent, or Firm*—Dean E. Carlson; Frank H. Jackson; James W. Weinberger

[57] ABSTRACT

A process for the nondestructive testing of ceramic objects to detect the presence of defects and microcracks in the surface in which a solution of silver nitrate is applied to the surface of the object which penetrates into the surface defects, drying the object so that the silver nitrate remains in the defects, and preparing an X-ray radiograph whereby any defects and microcracks will appear in the radiograph.

4 Claims, No Drawings

PROCESS FOR THE DETECTION OF MICRO-CRACKS

CONTRACTUAL ORIGIN OF THE INVENTION

The invention described herein was made in the course of, or under, a contract with the UNITED STATES DEPARTMENT OF ENERGY.

BACKGROUND OF THE INVENTION

This invention relates to a method of nondestructive testing. More specifically, this invention relates to a method for the non-destructive detecting of defects such as micro-cracks in the surface of objects made of ceramic materials There is a need to develop materials like ceramics for high-temperature applications, such as for turbine engine components. Ceramic materials that do not necessarily require cooling can be used to decrease fuel consumption and improve engine operating efficiencies. Furthermore, ceramic materials are often less costly then metals, more corrosion resistant, and are normally fabricated from abundant elements.

Nondestructive evaluation techniques such as ultrasonic, penetrating radiation or optical techniques are capable of detecting flaws such as cracks, porosity and nonbonding in ceramic components as well as variations in material properties such as density and elastic moduli. The application of these techniques can help ensure reproducible mechanical and physical properties, thus improving ceramic processing techniques and operational reliability.

Flaws approaching critical sizes in ceramics can be detected in geometrically simple objects under ideal conditions. Critical flaw sizes may vary with the particular material but have been estimated to be about $10\mu$ in hotpressed silicon nitride and about $100\mu$ in reaction bonded components. While flaws in geometrically simple objects can be detected under ideal conditions, components with complex geometries still cannot be inspected adequately.

Ceramic components may fail by the propagation of existing flaws to critical size. Thus determination of initial defect distribution and flaw characteristics in a component is important. The defects that are necessary to detect are pores, inclusions, cracks and large grains. Flaws with dimensions of 10 to $100\mu$ must be detected in ceramic components such as silicon nitride if they are to operate as structural materials in high-temperature environments, i.e. up to 1400° C., and at stresses up to 300 MPa. This flaw size is a few orders of magnitude smaller than critical flaw sizes in metal.

Methods for detecting micro-cracks which were investigated included the use of ultrasonics, acoustic emission, holographic interferometry and acoustic microscopy. None of these methods were found to be completely satisfactory. For example, it is not possible to consistently detect the presence of micro-cracks in the components. Furthermore, the cost of handling and applying the detection method, when thousands of individual pieces must be inspected, is prohibitive.

Other methods for detecting surface defects include the use of surface penetrants containing dyes and the use of radiation. Penetrants, however, are generally not capable of resolving flaws with critical dimensions less than about $300\mu$ and provide no information at all concerning flaw depth. The resolution of conventional X-ray systems is about $100\mu$, which can, however, be improved with more sophisticated electron focusing techniques. The biggest problem with X-rays is image contrast which is determined by the relative values of the absorption coefficients of the flaw and the material. In general, microcracks, i.e. cracks down to about $10\mu$ wide in ceramic materials, are difficult if not impossible to detect, since the X-ray beam must be exactly parallel to the crack plane in order to see the flaw.

PRIOR ART STATEMENT

The following published article is related to the subject matter but does not teach or suggest the present invention.

H. Berger, Practical Applications of Neutron Radiography and Gaging, ASTM Special Technical Publication 586, American Society for Testing and Materials, Philadelphia, Pa. (1976) teaches the use of a solution of gadolinium nitrate, acetone, and a wetting agent as a penetrant for detecting cracks in stainless steel using neutron radiography. However, it was not possible using this method to obtain sufficient resolution to detect micro-cracks of the size which must be detected. Furthermore, available neutron radiation sources are rare, and the use of such sources for the nondestructive detection of large quantities of ceramic or plastic objects would be prohibitively expensive. A number of known X-ray enhancing agents were investigated such as 3,5-diacetamido-2,4,6-triiodobenzoic acid and meglumine iodipamide as was a suspension of lead oxide in alcohol. However, none of the materials were able to provide the resolution necessary to detect micro-cracks down to about 10 to $20\mu$ in width in ceramic materials.

SUMMARY OF THE INVENTION

It has been found that, by applying a solution of a silver nitrate to the surface of ceramic bodies, it is possible to obtain sufficient resolution in an X-ray radiograph to detect defects and cracks in the surfaces down to about $10-20\mu$ wide. Thus the invention for the detection of micro-cracks in the surface of ceramic objects consists of applying a solution of silver nitrate to the surfaces of the object so that the solution penetrates cracks and defects in the surface, drying the solution whereby the silver nitrate remains in the cracks, and X-raying the object to prepare a radiograph whereby cracks and defects in the surface are visible in the radiograph.

The process of the invention has a number of advantages over other techniques for the detection of micro-cracks. For example, any silver nitrate adhering to the object after the radiograph can be easily removed by washing and/or ultrasonic cleaning. Objects of complex shapes or which have hidden inner surfaces not readily visible can be easily tested by the method of this invention since the solution can penetrate into cracks in inner surfaces so that they will become detectable in a radiograph. Furthermore, the method is relatively inexpensive to utilize and is readily adaptable for use in the nondestructive testing of large batches of objects at one time whereas most other methods must be applied to objects on an individual basis.

It is therefore an object of the invention to provide an improved method for the nondestructive testing of ceramic objects.

It is another object of the invention to provide an improved method for the nondestructive testing of ceramic objects which have complex shapes or hidden inner surfaces.

Finally, it is the object of the invention to provide an improved method for the nondestructive testing of ceramic objects in order to detect surface micro-cracks about $10\mu$ in width and to provide a method which is suitable for the testing of large quantities of objects.

DESCRIPTION OF THE PREFERRED EMBODIMENT

These and other objects of the invention for detecting micro-cracks and other defects in the surface of ceramic objects may be met by applying an aqueous solution containing from about 45 to 55 weight percent silver nitrate and about 0.25 to 0.75 weight percent of a wetting agent to the surface of the object, so that the solution penetrates into any cracks or defects in the surface of the object; drying the object so that the silver nitrate remains in the cracks and defects; and preparing an X-ray radiograph of the object whereby any cracks and defects in the surface of the object are detectable in the radiograph.

While the process of the invention was developed for use with silicon nitride and silicon carbide, it is suitable for use with any refractory ceramic material which is transparent to X-rays and which has an X-ray absorption coefficient which differs sufficiently from that of silver nitrate to provide the resolution necessary to detect surface defects and microcracks. The process will also be useful for the detection of cracks in the surface of material made from any of the various plastics. While silver nitrate was found to be particularly suitable for use with the refractory ceramic materials, it is entirely possible that other soluble compounds of radio-opaque material may work as well.

The solution may contain from 30 to 75 weight percent silver nitrate, preferably 45 to 55 weight percent, while 50 weight percent is especially preferred. It is desirable that the solution be as concentrated as possible in order that a sufficient amount of silver nitrate penetrate the cracks to provide the best contrast and resolution. However, a solution which is too concentrated will have a high viscosity which will prevent complete penetration of the crack. The solvent may be any liquid in which the silver nitrate is readily soluble such as water or alcohol. It is also preferred that an aqueous solution contain up to about 1% by weight of a surfactant or a wetting agent such as a detergent or a photo-wetting agent in order to promote penetration of cracks by the solution.

The silver nitrate solution may be applied to the object by any convenient method such as spraying or brushing. Preferably the solution is applied by immersing the objects into the solution so that sufficient solution is available to penetrate any surface cracks including any which may be in surfaces not normally visible. The object is preferably dried before X-raying to remove any solution from the surface and to concentrate the silver nitrate in the cracks and defects. One convenient method of application is to dip the objects into a hot (80–90° C.) aqueous solution so that the liquid would dry rapidly when the object was removed from the solution.

The method of this invention, using a 50 weight percent silver nitrate solution is alcohol or water has been found suitable for detecting micro-cracks down to 10 to 20 microns in width in silicon nitride and silicon carbide. Because the surface tension of the solution is low in order to penetrate micro-cracks, the technique may not provide adequate enhancement in wider cracks, i.e. over about $200\mu$, due to the lack of solution retention. However, cracks of this size are generally detectable by other methods. Furthermore, it is possible by this method to determine the depth of the surface cracks by proper alignment of the crack with the direction of the X-rays.

The X-ray radiograph can be prepared by any method well known to those skilled in the art of radiography. While X-rays having any practical energy can be used, some enhancement of crack detection has been noted when using X-rays having an energy range from 50 to 80 kev.

EXAMPLE I

To demonstrate the enhancement technique, a layer of silver nitrate nominally 0.05 mm thick was placed on a 3.8 mm thick flat plate of heat-processed silicon nitride. A radiograph was made using 80 kev X-rays with a source-to-film distance of 100 cm and employing type SR Kodak film. An inspection of the radiograph showed that although the thickness of silver nitrate represented an increase in thickness of 1.3%, the film density increased by almost 10%.

EXAMPLE II

A short piece of silicon carbide tubing, 25 mm in diameter with a wall thickness of from 1.5 to 3.0 mm and known by conventional x-radiography techniques to contain one crack was cleaned in an ultrasonic bath and dipped into a 80 to 90° C. solution of 50 weight percent silver nitrate in water containing several drops of Photoflow ® as a wetting agent. After a few seconds, the tube was removed, dried, and X-rayed with an energy of 80 kev onto type S R Kodak film.

Inspection of the resulting radiograph revealed five cracks. After sectioning, only the five cracks could be observed microscopically (100 x). These ID cracks penetrated about halfway through the wall (25 u deep), were tight (10 u wide), and several were slanted with respect to the tube axis. The tightness and skew prevented detection by ordinary radiography.

As can be seen by the previous discussion and examples, the process of this invention provides a quick, relatively inexpensive and effective method for the non-destructive detection of micro-cracks in solid materials, particularly those prepared from ceramics.

The embodiments of the invention in which an exclusive property or privilege is claimed are defined as follows:

1. A process for detecting defects and micro-cracks in the surface of ceramic objects comprising:
   applying a solution of silver nitrate to the surface of the object so that the solution penetrates any defects and cracks in the surface of the object,
   drying the object whereby the silver nitrate remains in the cracks and defects, and
   preparing an X-ray radiograph of the object whereby any defects and cracks in the surface of the object are visible in the radiograph.

2. The process of claim 1 wherein the solution contains 30 to 75 weight percent silver nitrate and up to 1 weight percent of a surface tension reducing agent.

3. The process of claim 2 wherein the solution contains 45 to 55 weight percent silver nitrate.

4. The process of claim 3 wherein the solution is applied by immersing the object in the solution.

* * * * *